United States Patent [19]

Piper et al.

[11] 4,172,200

[45] Oct. 23, 1979

[54] PROCESS FOR THE PREPARATION OF 10-DEAZAAMINOPTERIN AND RELATED COMPOUNDS

[75] Inventors: James R. Piper; John A. Montgomery, both of Birmingham, Ala.

[73] Assignee: Southern Research Institute, Birmingham, Ala.

[21] Appl. No.: 915,584

[22] Filed: Jun. 15, 1978

[51] Int. Cl.² .............................. C07D 475/08
[52] U.S. Cl. ................... 544/260; 542/458; 544/244
[58] Field of Search .................. 544/260; 542/458

[56] References Cited

U.S. PATENT DOCUMENTS 4,077,957  3/1978  Piper et al. .................... 544/260

Primary Examiner—Paul M. Coughlan, Jr.
Attorney, Agent, or Firm—Roylance, Abrams, Berdo & Farley

[57] ABSTRACT

There is disclosed an improved process for the preparation of 10-deazaaminopterin and related compounds. In accordance with this process, 6-(bromomethyl)-2,4-pteridinediamine hydrobromide is reacted with triphenylphosphine to form a phosphonium salt which is then treated with a base to yield the corresponding ylid (2,4-diamino-6-pteridinyl)methylenetriphenylphosphorane. This compound is reacted with an aromatic aldehyde such as diethyl 4-formylbenzoyl-L-glutamate to form an olefin which is then reduced catalytically to the tetrahydro derivative of the desired product. Oxidation of the tetrahydro derivative is accomplished with hydrogen peroxide.

12 Claims, No Drawings

PROCESS FOR THE PREPARATION OF 10-DEAZAAMINOPTERIN AND RELATED COMPOUNDS

This invention relates to an improved process for the preparation of 10-deazaaminopterin and related compounds.

Powerful dihydrofolic reductase inhibitors such as methotrexate are well known to have antimicrobial and antitumor activities. Such compounds are useful in the suppression and treatment of acute leukemia and related conditions. They have as their principal mechanism of action a competitive inhibition of the enzyme folic acid reductase. Folic acid must be reduced to tetrahydrofolic acid by this enzyme in the process of DNA synthesis and cellular replication. Methotrexate inhibits the reduction of folic acid and interferes with tissue-cell reproduction. Actively proliferating tissues, such as malignant cells, bone marrow, etc. are in general more sensitive to this effect of a dihydrofolic reductase inhibitor. Cellular proliferation in malignant tissues is greater than most normal tissue and thus these compounds may impair malignant growth without irreversible damage to normal tissues.

DeGraw et al, J. Med. Chem., 17, 552 (1974) describe 10-deazaaminopterin as having powerful antifolate activity and compares it with methotrexate. DeGraw et al also report that tetrahydro 10-deazaaminopterin is a potent antifolate. Sirotnak et al, AACR Abstracts, 18, 37 (1977) state that 10-deazaaminopterin was more active than methotrexate in all of the ascites tumor systems examined. It has also been reported that 10-deazaaminopterin was substantially more active than methotrexate following subcutaneous administration in mice in three out of five ascites tumors and two out of three solid tumors.

The only synthesis of 10-deazaaminopterin described in the literature involves a multiple step reaction process requiring 12 separate reactions followed by purification by column chromatography. Thus, DeGraw et al, J. Heterocycl Chem., 8, 105 (1971), show the synthesis of the p-carboxyphenylamino ketone semicarbazone, which is the side chain intermediate for the preparation of 10-deazaaminopterin, starting with 4-formylbenzoic acid. This synthesis involves five separate reactions. DeGraw et al, J. Med. Chem., 14, 866 (1974), describe the use of the p-carboxyphenylamino ketone semicarbazone to synthesize 4-amino-4-deoxy-10-deazapteroic acid. This synthesis involves four separate reactions. DeGraw et al, J. Med. Chem., 17, 552 (1974) show the conversion of 4-amino-4-deoxy-10-deazapteroic acid to 10-deazaaminopterin by coupling with glutamic acid. This requires three separate reactions to accomplish, followed by column chromatography.

It is an object of this invention to provide a new and improved process for the preparation of 10-deazaaminopterin and related compounds.

In accordance with the practice of this invention, 6-(bromomethyl)-2,4-pteridinediamine hydrobromide (I), prepared as described by Piper et al, J. Org. Chem., 42, 208 (1977) and in U.S. Patent Nos. 4,077,957 and 4,079,056, is reacted with triphenylphospine to form the phosphonium salt II. The phosphonium salt II is treated with a base, e.g., sodium methoxide, to yield the corresponding ylid (2,4-diamino-6-pteridinyl)methylenetriphenylphosphorane (III). This compound is reacted with an aromatic aldehyde in which the aldehyde group is attached to a carbon atom in the aromatic ring. Preferably, the aromatic aldehyde is mononuclear and has the formula:

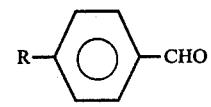

wherein R may be H, $CO_2H$, $CONHCH(CO_2R^1)(CH_2)_2CO_2R^2$ or $CONHCH(CO_2H)(CH_2)_2CO_2H$ in which $R^1$ and $R^2$ may each be a lower alkyl group, e.g., methyl, ethyl, propyl, butyl, etc. By "lower alkyl group" is meant a group containing up to six carbon atoms. The product is an olefin (IV). These reactions are preferably conducted in an anhydrous inert solvent, such as N,N-dimethylacetamide.

The olefin (IV) is reduced to form the corresponding tetrahydro derivative (V) of the desired product. Reduction may be accomplished by hydrogenation in the presence of $PtO_2$ catalyst or by other methods known in the art. The tetrahydro derivative (V) is then oxidized as by treating it with hydrogen peroxide or other known oxidizing agent to obtain the product (VI).

The process of this invention is illustrated by the following reaction sequence wherein the Roman numerals identify the same compounds which they identify in the foregoing description.

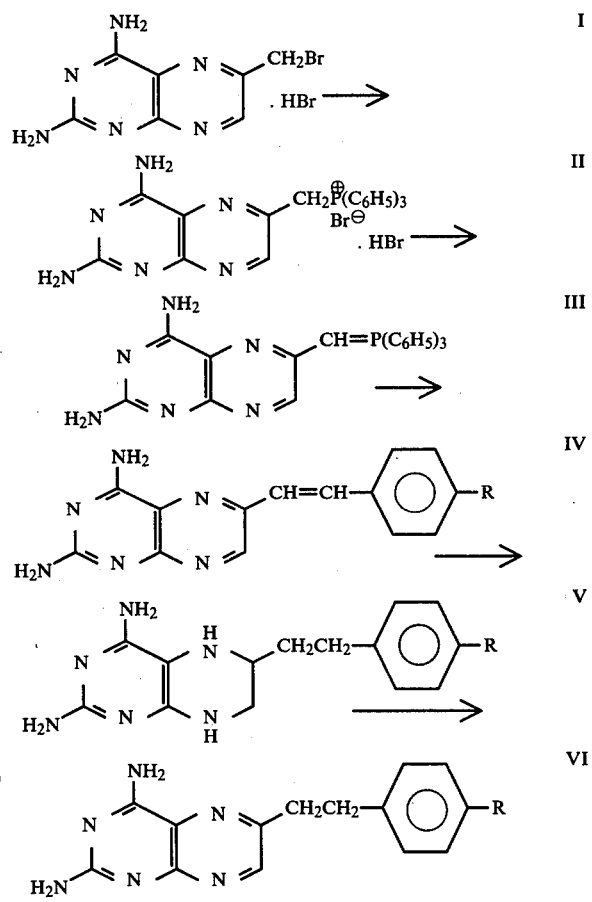

a: R = H
b: R = $CO_2H$
c: R = $CONHCH(CO_2Et)(CH_2)_2CO_2Et$
d: R = $CONHCH(CO_2H)(CH_2)_2CO_2H$

The following examples illustrate the best modes known for carrying out this invention:

EXAMPLE 1

2,4-Diamino-6-styrylpteridine (IVa). Equimolar amounts of I and triphenylphosphine were stirred in dry N,N-dimethylacetamide ($Me_2NAc$) (5 ml. per mmole of I), and the mixture was warmed (with exclusion of moisture) to 60° C. A clear pale-yellow solution formed while the mixture was stirred at 55–60° C. for 90 minutes. Partial separation of crystalline phosphonium salt II occurred toward the end of the heating period. The resulting mixture was cooled to 25° C., and solid sodium methoxide (2 mmoles per mmole of II used) was added in one portion with rapid stirring. A crimson solution formed within 5 minutes; continued stirring for 5–10 minutes longer led to separation of a crimson solid, ylid III. After 30 minutes, benzaldehyde (10% excess) was added. The color faded and the mixture thinned markedly within 15 minutes. After 3 hours stirring at ambient temperature, the mixture was filtered from the small amount of remaining yellow-orange insoluble matter. [Mass spectral examination of this solid revealed it to be mainly the unchanged ylid III, m/e 436 (M+).] Addition of water to the filtrate caused precipitation of the predominant product IVa as a yellow solid; mass spectrum, m/e 264 (M+) with no evidence for the presence of unchanged III.

EXAMPLE 2

4-[2-(2,4-Diamino-6-pteridinyl)vinyl]benzoic Acid (IVb). A partial solution of the ylid III in $Me_2NAc$ prepared as described in Example 1 was treated with 4-formylbenzoic acid. The crimson color faded rapidly as the mixture became thick with yellow-orange precipitate. Stirring at ambient temperature was continued for 3 hours before most of the $Me_2NAc$ was removed by evaporation in vacuo. The residue was then stirred with water and the water insoluble solid was collected by filtration and washed with benzene foflowed by ethyl ether and dried in vacuo. The solid was then stirred with warm aqueous ammonium hydroxide solution and the mixture was filtered. Addition of acetic acid to the filtrate to produce pH 4–5 caused precipitation of IVb as a pale-yellow solid; mass spectrum, m/e 308 (M+).

EXAMPLE 3

Diethyl N-[4-[2-(2,4-Diamino-6-pteridinyl)vinyl]benzoyl]-L-glutamate (IVc). The required carbonyl compound, diethyl 4-formylbenzoyl-L-glutamate, was prepared essentially as described by J. B. Hynes and C. M. Garrett [J. Med. Chem., 18, 632 (1975)], except that $CHCl_2$ instead of pyridine was used as the reaction solvent. The ylid III was prepared (on a 3.0 mmole scale) as described in Example 1, and diethyl 4-formyl-benzoyl-L-glutamate (3.0 mmoles) was added. Rapid disappearance of the dark-red color and thinning of the reaction mixture occurred within 5 minutes. The mixture was stirred at 25° C. for 4 hours before the insoluble material was removed by filtration. $Me_2NAc$ was removed from the filtrate by evaporation in vacuo, and the residue was stirred with benzene. The benzene-insoluble solid was collected, washed with ethyl ether and air dried to give crude IVc (1.0 g.). Mass spectral analysis of this material revealed the expected peak of m/e 493 (M+) and showed the absence of unchanged ylid III. The solid was then dissolved in $Me_2NAc$ (5 ml.) at 25° C., and the solution was treated with a small amount of decolorizing charcoal and filtered through a mat of diatomaceous earth. Addition of water to the clear filtrate caused precipitation of IVc as a yellow solid, which was collected by filtration, washed with water and dried in vacuo at 25° C. over $P_2O_5$; yield 0.67 g. Spectral data: $^1H$ NMR (in $Me_2SO-d_6$), two triplets with centers near δ1.2 (6 protons, $OCH_2C\underline{H}_3$), complex multiplet centered near 2.1 (4 protons, $CHC\underline{H}_2C\underline{H}_2CO$), two quartets centered near 4.1 (4 protons, $OC\underline{H}_2CH_3$), multiplet centered near 4.4 (1 proton, $NHC\underline{H}CH_2$), singlet at 6.8 (2 protons, $NH_2$), broad complex multiplet from 7.2-8.3 (8 protons, CH=CH, $NH_2$, and $C_6H_4$), doublet centered near 8.7 (1 proton, CONH), singlet at 8.9 (1 proton, pteridine $C_7$-H).

EXAMPLE 4

10Deazaminopterin (VId). $PtO_2$ catalyst (40 mg. of 84% purity) suspended in glacial acetic acid (10 ml.) was hydrogenated under ambient conditions until $H_2$ uptake ceased (8 ml. required). Compound IVc (200 mg., 0.405 mmoles) was then added to the suspension of Pt in acetic acid, and hydrogenation at ambient conditions (25° C. and 745 mm. Hg. pressure) was conducted over a period of 19 hours. The uptake of $H_2$ ceased at 29 ml., which corresponds to 3 mmoles of $H_2$ per mmole of IVc. The yellow solution was filtered from the catalyst through a mat of diatomaceous earth, and the catalyst and mat were washed with acetic acid until the washings were colorless. The filtrate was evaporated under reduced pressure (water aspirator, rotary evaporator, bath to 35° C. maximum) to give a viscous red-orange gum. This residue was twice dissolved in ethyl alcohol (10 ml.), and each time the solution was evaporated as above to aid in removal of acetic acid. The residue was then dissolved in a solution consisting of ethyl alcohol (6 ml.) and 0.5 N NaOH (4 ml.). The resulting yellow solution was stirred at 25° C. while exposed to air for 20 hours and then evaporated (water aspirator, bath at 20°–25° C.) until the ethyl alcohol had been removed. The aqueous solution that remained was diluted with water (to about 20 ml.) and filtered to ensure clarity through a mat consisting of a layer of diatomaceous earth and a layer of powdered cellulose, each about 3 mm. thick in a 15-ml. Buchner funnel. The mat was washed with water until the washings were colorless. The filtrate, now 30 ml. in volume, was a clear, yellow solution of pH 10.2. A 1-ml. portion of this solution was treated with acetic acid to lower the pH to 4. The pale-yellow solid that formed was collected by filtration and subjected to field-desorption mass spectral analysis. The sample produced peaks of m/e 440 and m/e 442, which correspond to the $(M+1)^+$ ions for the sought product VId and a dihydro form. This analysis showed that extensive oxidation of the reduced pyrazine ring of the pteridine moiety had occurred during the ester-hydrolysis step. In order to effect complete regeneration of the heteroaromatic ring, the remaining main portion of the basic solution was treated with $H_2O_2$(0.50 ml. of 30%). After 1 hour, the solution was carefully treated with 1 N HCl to lower the pH to 3.5. Yellow solid precipitated, and, after the mixture had been kept in a refrigerator for 16 hours, was collected, washed thoroughly with water followed by ethyl ether, and dried in vacuo at 25° C. over $P_2O_5$; yield 100 mg. Mass spectral (field-desorption) analysis of this product revealed that complete reoxidation within the pteridine ring had been achieved as evidenced by absence of the peak of m/e 442 and continued presence of that of m/e 440. The UV absorption spectrum of this product agrees with that reported for VId prepared by a different synthetic route by J. I. DeGraw, R. L. Kisliuk, Y. Gaumont, C. M. Baugh, and M. G. Nair [J. Med. Chem., 17, 552 (1974)]. The structure of VId prepared by the present route is fully substantiated by its heretofore unreported $^1$H NMR spectrum, which is as follows: $^1$H NMR (in Me$_2$SO-d$_6$), multiplet centered near δ2.05 (2 protrons, CHC$\underline{H}$$_2$CH$_2$), multiplet centered near 2.35 (2 protrons, CH$_2$CO), singlet at 3.16 (4 protons, pteridinyl C$\underline{H}$$_2$C$\underline{H}$$_2$C$_6$H$_4$), multiplet centered near 4.40 (1 proton, NHC$\underline{H}$CH$_2$), singlet at 6.68 (2 protons, NH$_2$), two doublets centered near 7.35 and 7.80 (2 proprotons each, C$_6$H$_4$), singlet at 7.67 (2 protons, NH$_2$), doublet centered near 8.48 (1 proton, CONH), 8.58 (1 proton, pteridine C$_7$—H).

We claim

1. A process which comprises reacting 6-(bromomethyl)-2,4-pteridinediamine hydrobromide with triphenylphosphine to form the phosphonium salt thereof; treating said phosphonium salt with a base to yield the corresponding ylid (2,4-diamino-6-pteridinyl) methylenetriphenylphosphorane; and reacting said ylid with an aromatic aldehyde having the formula:

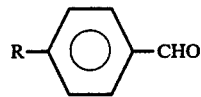

wherein R is a member selected from the group consisting of H, CO$_2$R$^1$ or CO$_2$H, CONHCH(CO$_2$R$^1$)(CH$_2$)$_2$CO$_2$R$^2$ or CONHCH(CO$_2$H)(CH$_2$)$_2$—CO$_2$H in which R$^1$ and R$^2$ may each be a lower alkyl group, to obtain a product having the formula:

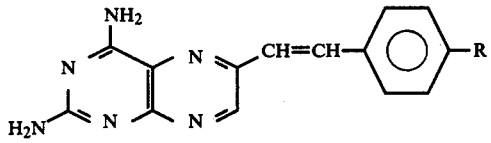

wherein R is the same as previously described.

2. A process as defined in claim 1 wherein R is hydrogen.

3. A process as defined in claim 1 wherein R is CO$_2$H or CO$_2$R$^1$ wherein R$^1$ is a lower alkyl group.

4. A process as defined in claim 1 wherein R is CONHCH(COR$^1$)(CH$_2$)$_2$CO$_2$R$^2$ wherein R$^1$ and R$^2$ are each a lower alkyl group.

5. A process as defined in claim 4 wherein R$^1$ and R$^2$ are each ethyl.

6. A process as defined in claim 1 wherein R is CONCH(CO$_2$H)(CH$_2$)$_2$CO$_2$H.

7. A process as defined in claim 1 wherein said reaction is conducted in an anhydrous inert solvent.

8. A process as defined in claim 1 wherein the product obtained by said process is reduced to form the corresponding tetrahydro derivative having the formula:

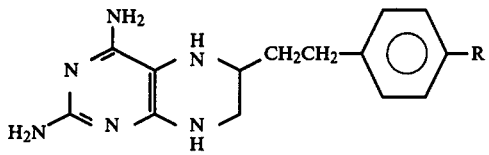

9. A process as defined in claim 8 wherein said reduction is accomplished by hydrogenation.

10. A process as defined in claim 8 wherein said tetrahydro derivative is oxidized to obtain a product having the formula:

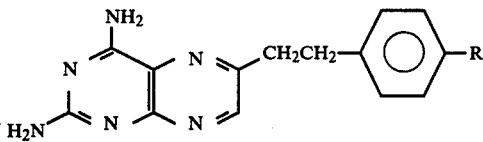

11. A process as defined in claim 10 wherein oxidation is accomplished by treating said tetrahydro derivative with hydrogen peroxide.

12. A process for the preparation of 10-deazaaminopterin which comprises reacting 6-(bromomethyl)-2,4-pteridinediamine hydrobromide with triphenylphosphine to form the phosphonium salt thereof; treating said phosphonium salt with a base to yield the corresponding ylid (2,4-diamino-6-pteridinyl)methylenetriphenylphosphorane; reacting said ylid with diethyl 4-formylbenzoyl-L-glutamate to form diethyl N-[4-[2-(2,4-diamino-6-pteridinyl)vinyl]benzoyl]-L-glutamate; hydrogenating and hydrolyzing said diethyl N-[4-[2-(2,4-diamino-6-pteridinyl)vinyl]benzoyl]-L-glutamate to yield the tetrahydro derivative of 10-deazaaminopterin; oxidizing said tetrahydro derivative and recovering said 10-deazaaminopterin.

* * * * *